United States Patent [19]

Cerola et al.

[11] Patent Number: 5,292,488
[45] Date of Patent: Mar. 8, 1994

[54] CATALYST SUPPORT ASSEMBLY FOR A CONTACT LENS STERILIZING APPARATUS

[75] Inventors: Joseph J. Cerola, Guntersville; Steven C. Perlaky, Arab, both of Ala.

[73] Assignee: Ciba Vision Corporation, Atlanta, Ga.

[21] Appl. No.: 716,703

[22] Filed: Jun. 19, 1991

Related U.S. Application Data

[60] Division of Ser. No. 631,759, Dec. 21, 1990, Pat. No. 5,196,174, which is a continuation of Ser. No. 364,471, Jun. 9, 1989, abandoned.

[51] Int. Cl.$^5$ ............................................. A61L 2/00
[52] U.S. Cl. ..................................... 422/292; 134/901; 206/5.1; 422/28; 422/30; 422/300; 422/301
[58] Field of Search .................... 422/28, 30, 300, 301, 422/292; 206/5.1, 205, 210; 134/901; 435/288

[56] References Cited

U.S. PATENT DOCUMENTS

| | | | |
|---|---|---|---|
| 3,063,083 | 11/1962 | Obitts | 206/5.1 |
| 3,770,113 | 11/1973 | Thomas | 206/5.1 |
| 3,912,451 | 10/1975 | Gaglia, Jr. | 422/30 |
| 3,939,968 | 2/1976 | Ryder | 206/5.1 |
| 4,011,941 | 3/1977 | Parsons | 206/5.1 |
| 4,013,410 | 3/1977 | Thomas et al. | 21/58 |
| 4,222,187 | 4/1980 | Thomas | 206/5.1 |
| 4,257,521 | 3/1981 | Poler | 206/5.1 |
| 4,396,583 | 8/1983 | Le Boeuf | 422/201 |
| 4,517,291 | 5/1985 | Seago | 435/14 |
| 4,637,919 | 1/1987 | Ryder et al. | 422/300 |
| 4,807,750 | 2/1989 | Ryder et al. | 206/5.1 |
| 4,817,998 | 4/1989 | Ryder et al. | 422/300 |
| 4,826,001 | 5/1989 | Castillo | 422/301 |
| 4,838,413 | 6/1989 | Monestere | 206/5.1 |
| 4,889,693 | 12/1989 | Su et al. | 422/300 |
| 5,059,402 | 10/1991 | Seamons et al. | 422/301 |

FOREIGN PATENT DOCUMENTS

| | | |
|---|---|---|
| 0155505 | 9/1985 | European Pat. Off. . |
| 2209845 | 5/1989 | United Kingdom ........... 422/295 |

*Primary Examiner*—Robert J. Warden
*Assistant Examiner*—Laura E. Collins
*Attorney, Agent, or Firm*—Trexler, Bushnell, Giangiorgi & Blackstone, Ltd.

[57] ABSTRACT

Apparatus is provided for use in the sterilization of contact lenses or the like, wherein lenses are disposed within a sterilizing solution contained within a reaction vessel, which sterilizing solution is capable of being decomposed through contact with a catalytic agent. The apparatus comprises a reaction vessel capable of containing a sterilizing solution and comprising a container portion, a cover and structure for supporting an article in contact with sterilizing solution in the container. Further structure is provided for mounting a catalytic agent on the supporting structure such that the catalytic agent is removable for replacement by a user as the catalytic agent becomes exhausted in use. The mounting of the catalytic agent on the article supporting structure prevents contact of the catalytic agent with the solution in the container until the article supporting structure with the contact lenses therein is placed in the solution in the container for beginning the sterilizing process, to thereby prevent premature breakdown of the sterilizing solution prior to the introduction of contact lenses for sterilization therein.

8 Claims, 5 Drawing Sheets

CATALYST SUPPORT ASSEMBLY FOR A CONTACT LENS STERILIZING APPARATUS

This is a divisional of copending application(s) Ser. No. 07/631,759 filed Dec. 21, 1990, now U.S. Pat. No. 5,196,174 which is a File Wrapper Continuation of Ser. No. 07/364,471 filed on Jun. 9, 1989, now abandoned.

BACKGROUND OF THE INVENTION

This invention relates to a chemical sterilization process for articles such as contact lenses. More particularly, the invention concerns an improved apparatus adapted to be employed in said chemical sterilization process.

The sterilization of contact lenses is currently done by a number of different processes. Some processes employ heat, either in a dry sterilization environment, or with a sterilized saline or similar solution. A further process has also been developed which employs an anti-microbial sterilizing solution such as hydrogen peroxide ($H_2O_2$).

The present invention concerns an apparatus specifically designed for use with the latter (hydrogen peroxide) type of sterilization technique. One particularly useful method and apparatus is disclosed in prior U.S. Pat. No. 4,013,410, also assigned to the assignee of this application, to which reference is invited for background material concerning this type of sterilizing process.

Briefly, the hydrogen peroxide solution which is employed is of a relatively weak concentration, for example, no more than on the order of 3% solution of hydrogen peroxide in water. In this sterilizing process it is important to insure that the hydrogen peroxide solution, or any remnants thereof, are completely absent from the lenses before the lenses are reinserted by the wearer. Accordingly, the heretofore applied processes operate to neutralize the hydrogen peroxide solution well before the lenses are removed from the apparatus and replaced in the eye of the wearer.

Generally speaking, the process employed by the above referenced patent uses a catalytic agent such as platinum, which will produce a chemical reaction resulting in neutralization or decay of the hydrogen peroxide. Essentially, a free oxygen molecule is liberated and the hydrogen peroxide is reduced to water. Preferably, the process is arranged to take place over a period of several hours of time, depending on the nature of the catalytic agent and the initial strength of the original sterilizing solution. Accordingly, it is generally recommended that the user employ the process overnight in order to assure full decomposition of the hydrogen peroxide and a considerable period of soaking of the lenses in the sterile water which remains of the solution after decomposition of the hydrogen peroxide.

While the apparatus employed in the above-referenced patent has met with commercial success, there is nonetheless room for further improvement. More particularly, one apparatus currently in use employs a plastic carrier member which is coated with a suitable platinum catalytic agent, and which is generally disposed in the bottom of a cylindrical container. The container is then filled with the hydrogen peroxide solution and the contact lenses, which are held in a further lens carrier/lens support case member, are then disposed within the container. Generally speaking, the lens support or lens carrier members are well-ventilated basket-like structures which are affixed to a cap member which in turn forms a cap or top closure for the solution-filled container. It is important, however, to provide some venting of the cap portion of the closure to control pressure buildup by permitting the escape of some of the free oxygen generated during the decomposition of the hydrogen peroxide solution.

While this system has proven highly successful in operation, there is, as mentioned above, room for improvement. For example, it is necessary for the user to periodically handle the "catalyst" which has the coating of catalyst material. That is, the catalyst material is consumed over a period of use, and therefore the catalyst member must be removed and replaced with a new catalyst from time to time. Handling by the consumer has a number of drawbacks. Some of the platinum coating of the carrier may rub off onto the fingers and cause undesirable staining of the skin and/or clothing of the user. Moreover, various proteins, salts, etc., from the skin might compromise the integrity and action of the catalyst. It appears that to some extent sulfur compounds and the proteins in the skin may combine with the platinum to form an inert compound. Moreover, with the catalyst member disposed in the bottom of the container, it is somewhat difficult to reach it manually without the use of some sort of tool, or the like.

There is also some concern that with the catalyst sitting in the bottom of the container between uses and after rinsing the container following a use, that some excess water may be trapped or entrained around the catalyst member which may give some potential for bacterial growth.

OBJECTS AND SUMMARY OF THE INVENTION

It is an object of the invention to provide an improved apparatus for use in the foregoing lens sterilization process which further improves upon some of the prior art apparatus discussed hereinabove.

Briefly, and in accordance with the foregoing discussion, the invention provides apparatus for use in the sterilization of contact lenses or the like, wherein said lenses are disposed within a sterilizing solution contained within a reaction vessel, which sterilizing solution is capable of being decomposed through contact with a catalytic agent. The apparatus in accordance with the invention comprises a reaction vessel capable of containing a sterilizing solution and comprising a container portion, cover means and means for supporting an article in contact with sterilizing solution in said container; and further including means for mounting a catalytic agent on said supporting means such that said catalytic agent is removable for replacement by a user as the catalytic agent becomes exhausted in use; said mounting of said catalytic agent on said supporting means thereby preventing contact of the catalytic agent with the solution in said container until the article supporting means with the contact lenses therein are placed in the solution in the container for beginning the sterilizing process, to thereby prevent premature breakdown of the sterilizing solution prior to the introduction of contact lenses for sterilization therein.

BRIEF DESCRIPTION OF THE DRAWINGS

The features of the present invention which are believed to be novel are set forth with particularity in the appended claims. The organization and manner of the operation of the invention, together with further objects and advantages thereof may best be understood by reference to the following description, taken in connection with the accompanying drawings in which like reference numerals identify like elements, and in which:

DETAILED DESCRIPTION OF THE ILLUSTRATED EMBODIMENT

Figure 1:
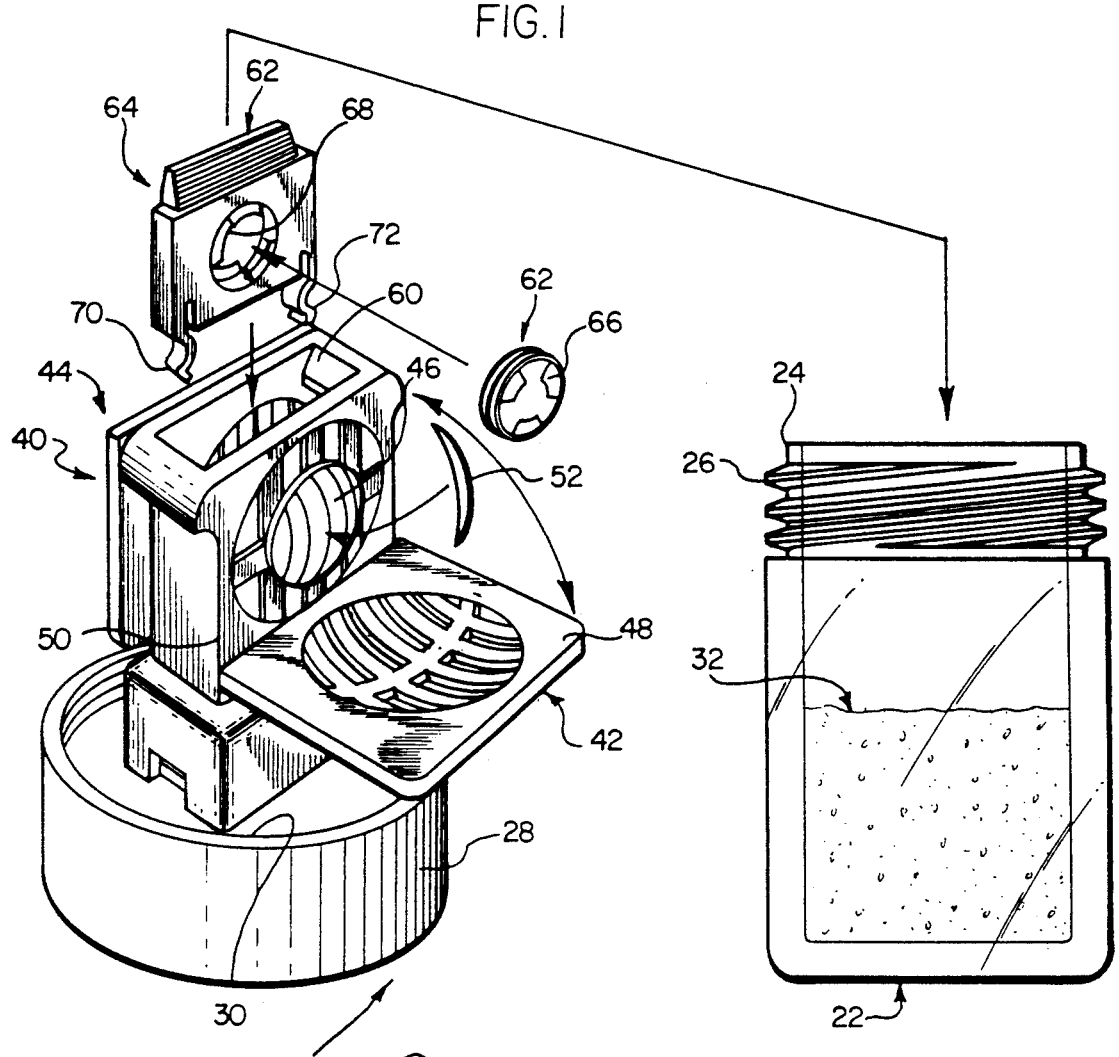
FIG. 1 is a partially exploded perspective view of apparatus in accordance with the invention.
Figure 2:
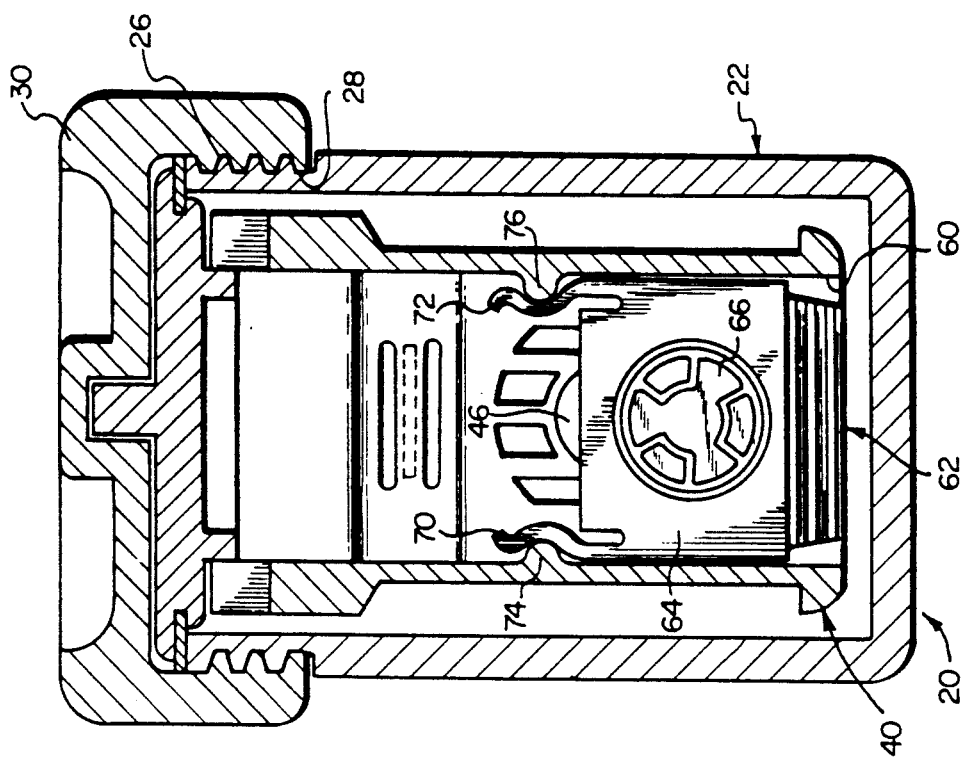
FIG. 2 is an enlarged sectional view of a fully assembled apparatus of the invention in operation for sterilizing contact lenses.
Figure 3:
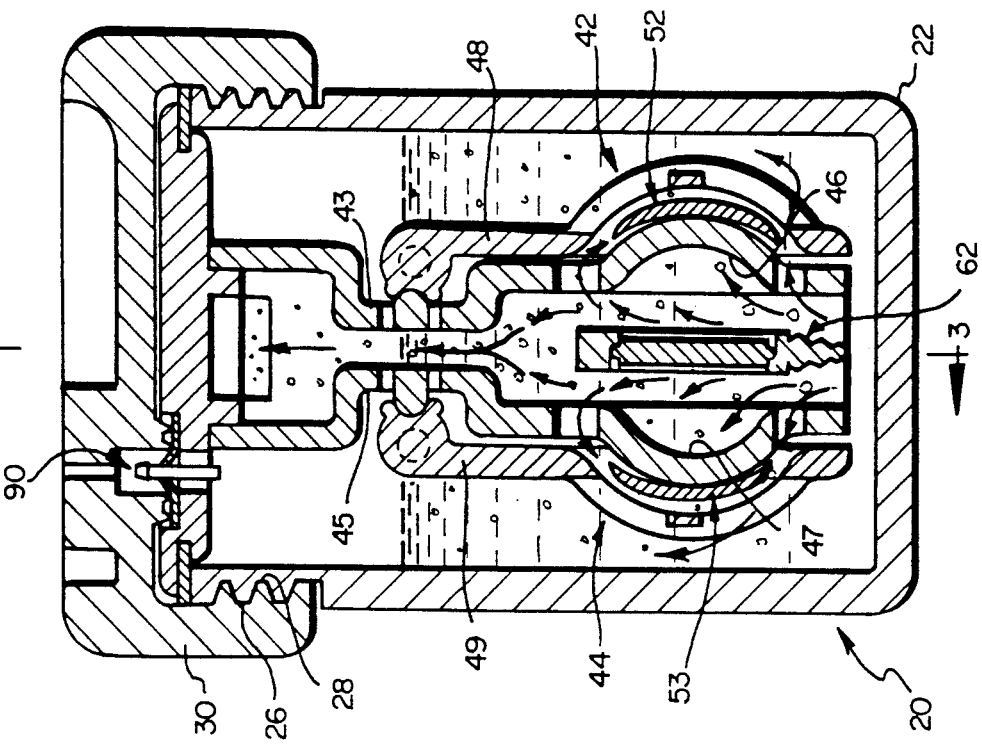
FIG. 3 is a reduced sectional view taken generally along the line 3—3 of FIG. 2.

Referring initially to FIGS. 1-3, the apparatus in accordance with the invention is designated generally by the reference numeral 20. Generally speaking, the apparatus 20 includes a container or reaction vessel 22, which is preferably generally cylindrical in shape and terminates in an open top 24 which preferably has a thread 26 formed thereupon for threadably engaging a complementary thread 28 formed within a cap member 30. This reaction vessel or container 22 is particularly adapted to contain a quantity of sterilizing solution 32, which preferably comprises hydrogen peroxide. In accordance with prevailing practice, the hydrogen peroxide is of a relatively low concentration, and preferably no more than a 3% solution of hydrogen peroxide in water. Different concentrations of hydrogen peroxide may be used in particular applications without departing from the invention.

In accordance with the customary practice, the cap member 30 also mounts a lens supporting structure or assembly designated generally by the reference numeral 40. The lens supporting structure 40 comprises a pair of basket-like lens-receiving or lens support structures 42, 44 which are substantially identical and oppositely facing. Each lens supporting structure comprises a base 43, 45 which includes a lens-supporting dome-like or semispherical member or portion 46, 47 and an overlying and complementary formed basket-like lid member 48, 49 which is preferably hingedly attached to a base or frame portion 50 from which the aforementioned lens support members 46, 47 projects.

Preferably, both the cover member 48, 49 and the lens support member or portions 46, 47 are formed of a lattice-like structure to promote flow of the fluid 32 therethrough and around contact lenses 52, 53 disposed therebetween when the cap 30 and depending lens support structure 40 are coupled with the container or reaction vessel 22. In this regard, it will be seen that the cap and lens support structure 30, 40 are illustrated in an inverted position in FIG. 1, such that in use the structure of FIG. 1 is inverted such that the threads of the cap 30 engage the threads 26 of the container 22 and such that the contact lenses, as indicated for example by reference numeral 52, are supported in a position depending from the cap and immersed within the fluid 32 in the container 22. Most of the foregoing structure is conventional in form, and need not be described in further detail herein.

Departing from convention, and in accordance with an important feature of the invention, the lens support or lens carrying structure 40 is further provided with an open-ended central interior receptacle or chamber 60. Within this receptacle 60 there is received a catalytic agent indicated generally by reference numeral 62 in a position substantially intermediate the contact lenses, e.g., 52, 53 supported within the basket-like structures defined by projection 46 and basketlike cover member 48. The mounting of the catalyst member 62 in this fashion substantially precludes any physical contact of the user with the catalytic agent during use; however, as will be seen later, the catalytic agent or catalyst member 62 is easily removable and replaceable when desired, as for example, when replacing a catalytic agent which has become exhausted from use.

Advantageously, the placing of the catalyst member or catalytic agent 62 within the lens support structure in this manner achieves two important ends. Firstly, this arrangement substantially prevents contact of the catalyst material by the user, thereby preventing any undesirable effect on the catalyst, for example the formation of an inert compound on the catalyst agent as a result of contact with sulfur compounds and proteins in the skin. As a second important matter, the placement of the catalyst or catalytic agent in the lens carrying structure prevents the catalyst from coming into contact with the solution 32 until the user has completed the placement of the lenses within the lens support structure, inverted the cap and lens support structure, and placed the same within the container 22 to begin the sterilization process.

In some prior art apparatus, a catalyst member is placed directly into the container 22, thus beginning the breakdown of the sterilizing solution prior to the actual introduction of the contact lenses for sterilization therein. In the event the user elects to fill the container 22, with the catalyst in place therein, with the sterilizing solution 32 prior to completing the placement of the contact lenses on the lens support structure, or in the event of any other delay between the beginning of contact of the catalyst with the solution and the actual placement of the lens carrying structure within the container 22, the breakdown of the sterilizing solution may be undesirably accelerated. Accordingly, the structure of the present invention helps to insure a maximum time of contact of the lenses with a maximum strength sterilizing solution initially, and avoids a premature breakdown of the sterilizing solution due to premature contact with the catalyst or catalytic agent.

In a preferred embodiment illustrated in FIGS. 1-5, the means for mounting the catalyst or catalytic agent within the lens support structure further comprises a carrier member 64 which has an enlarged, frame-like body. A disc-like catalyst carrying member or portion or "disc" 66 receives a quantity of catalyst material thereon; for example, by a sputter coating or other deposition process. The disc 66 is complementary in form for being releasably supported and mounted upon the frame-like member 64 and, more particularly, within a complementary opening 68 formed in the frame-like member 64.

Figure 4:
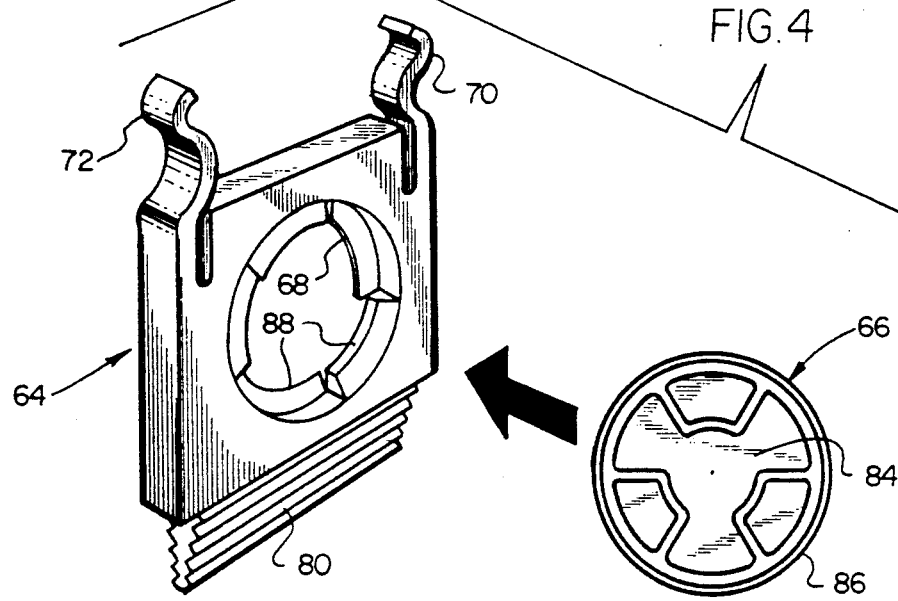
FIG. 4 is an enlarged exploded perspective view illustrating a frame-like carrier member and a disc-like catalyst member in accordance with a preferred form of the invention.
Figure 5:
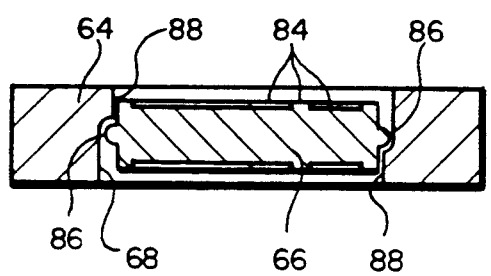
FIG. 5 is a transverse section taken on the assembled carrier and catalyst members of FIG. 4.
Figure 8:
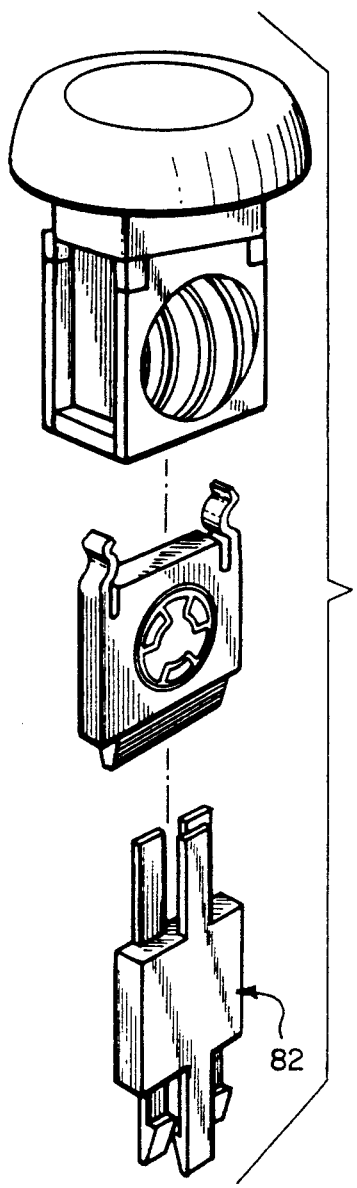
FIG. 8 is an exploded perspective view illustrating the assembly of the catalyst member and carrier member with the lens support assembly utilizing a specialized tool in accordance with an alternate form of the invention.
Figure 10:
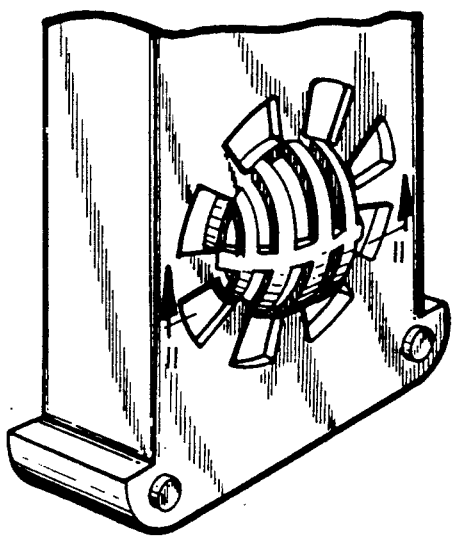
FIG. 10 is an enlarged partial perspective view of a portion of the lens support structure in accordance with a preferred form of the invention.
Figure 11:
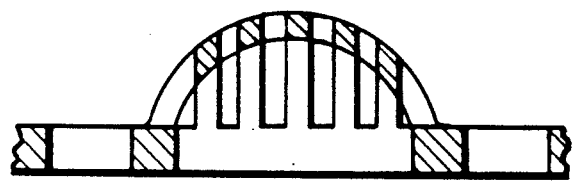
FIG. 11 is a sectional view taken generally along the line 11—11 of FIG. 10.
Figure 9:
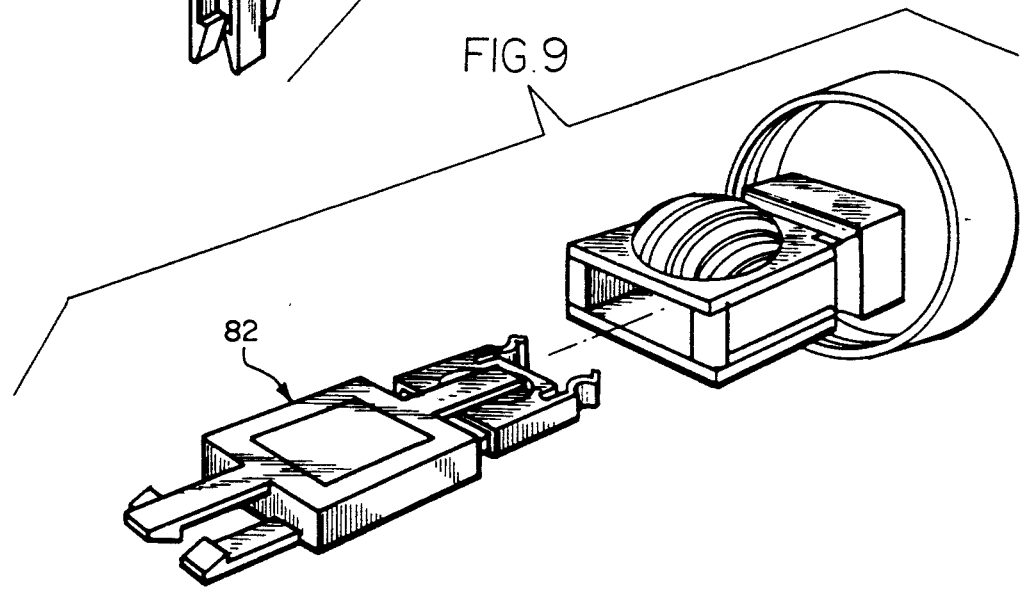
FIG. 9 shows a further step in the assembly indicated in FIG. 8.

Referring now briefly to FIGS. 4 and 5, it will be seen that the frame-like carrier member 64 includes a pair of resilient clip-like engaging or locking members 70, 72. Cooperatively, an interior portion of the receptacle 60 includes complementary mating projections 74, 76 for releasably engaging the resilient clip-like engaging members. Preferably the frame-like carrier member 64 also includes a projecting and preferably serrated gripping portion 80 which may be gripped by the user for inserting and/or removing the same relative to the receptacle 60. Alternatively, as shown in FIGS. 8 and 9, a separate insertion/removal tool 82 may be provided for this purpose.

As best viewed in FIGS. 4 and 5, and in accordance with a preferred form of the invention, the catalyst disc 66 comprises a generally flat, disc-like member with a pattern of recesses and ridges 84 formed on either face or surface thereof. These recesses and ridges generally aid in the process of manufacture and plating or coating of the disc member 66 with catalyst. In order to secure the disc 66 within the complementary opening 68 in carrier 64, a projecting annular rim 86 is formed around the periphery of the disc 66. This rim 86 is engaged by a series of tabs 88 which project from alternate sides of the opening 68 in the embodiment illustrated in FIGS. 4 and 5, to provide for a snapping engagement therebetween when the disc is inserted from either side.

As best viewed in FIG. 2, the cap 30 is also provided with a venting structure designated generally by the reference numeral 90, which is the same as the venting structure which is more fully disclosed and described in copending application of R. W. Kanner et al, Ser. No. 268,053 filed Nov. 7, 1988 which is commonly owned with this application, and to which reference is invited concerning further details of the venting structure 90. Venting structure 90 permits the buildup of a controlled amount of pressure due to the release of oxygen in the decomposition of the hydrogen peroxide. While this oxygen is not necessarily vented through the venting structure 90, excess pressure in the vessel is nonetheless prevented by the release of some amount of the residual air and/or added oxygen in the space between the level of filling of the container with hydrogen peroxide and the cap.

Figure 12:
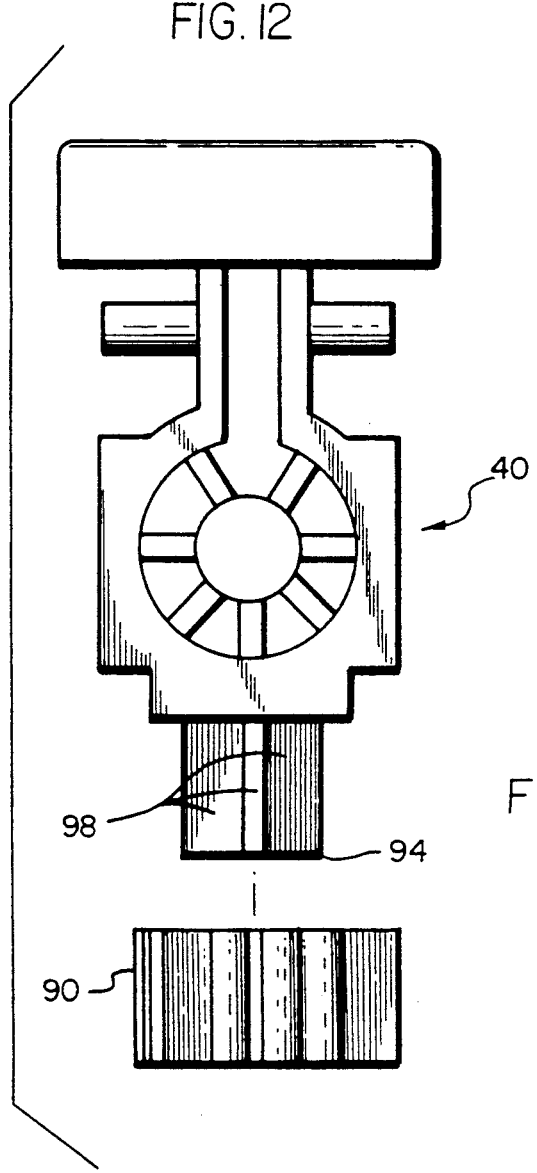
FIG. 12 is a partially exploded elevational view showing an alternate form of catalyst member and catalyst carrier portion of the lens carrier and support assembly, in accordance with an alternate form of the invention.
Figure 13:
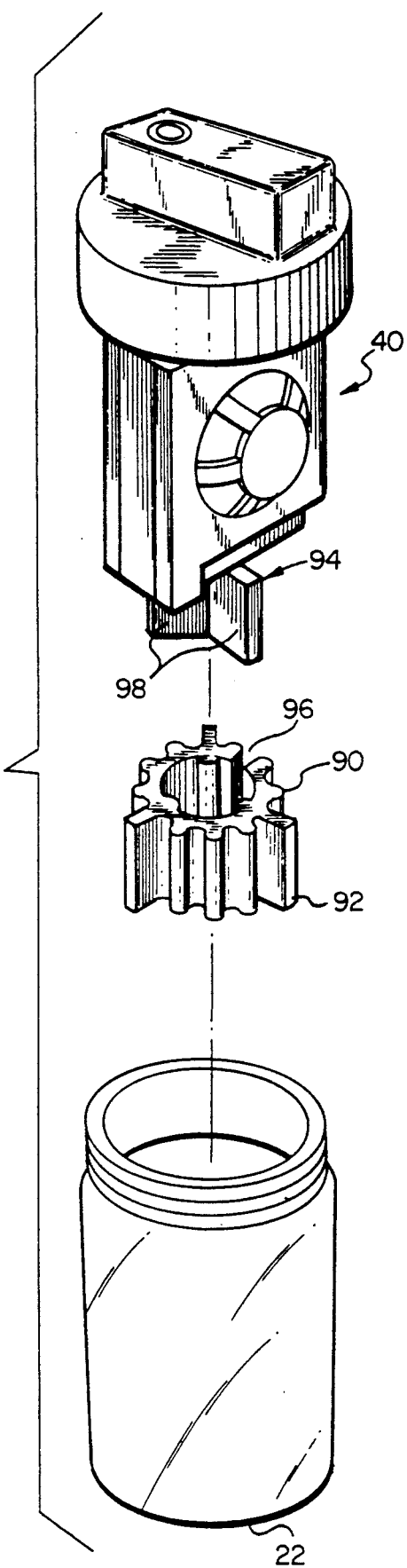
FIG. 13 is an exploded perspective view indicating assembly of the catalyst, lens carrier and container portion in accordance with the embodiment of FIG. 12.
Figure 14:
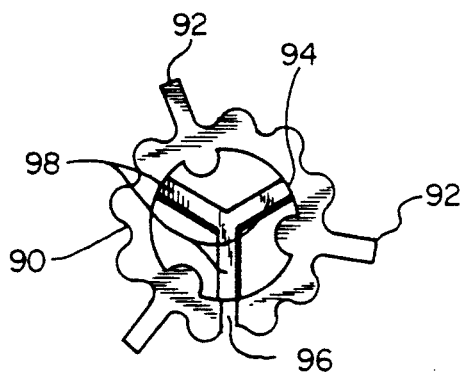
FIG. 14 is a bottom plan view showing the catalyst member configured in accordance with FIGS. 12 and 13 assembled with the lens carrier assembly.

Referring next to FIGS. 12-14, an alternative embodiment of the mounting means on the lens carrier structure for receiving a catalyst member or catalytic agent is shown. In the embodiment of FIGS. 12-14, the catalytic agent is similar if not identical in form to a presently used catalytic agent and comprises a generally hollow, and circular, cogwheel-shaped body 90. The body 90 is shaped to cooperatively fit within the bottom portion of the cylindrical container 22. To this end the cogwheel-shaped body 90, as best viewed in FIGS. 13 and 14 has three radially outwardly projecting spines 92 which serve to position the body 90 relative to the interior walls of cylindrical container 22.

Departing from conventional practice, the body 90 is not placed within the container 22 by the user. Rather, the lens supporting structure 40 is provided with an additional projecting catalyst-engaging portion 94 which engages with and carries the catalyst member 90. In this regard the catalyst member 90 has a small gap or opening 96 therein, which imparts a somewhat resilient nature thereto, such that the catalyst member 90 may be resiliently expanded somewhat to interfit over the projection 94 in a friction-type fit. In the embodiment illustrated in FIGS. 12-14, the projecting member 94 is a three-legged member having three substantially equal and equi-angularly spaced radial projections 98, which are dimensioned for gripping engagement with an interior surface of the catalyst member 90. Accordingly, the catalyst member 90 is engageable with the projection 94 so as to be carried upon the lens support structure 40, such that the catalyst will not be introduced into the solution within container 22 prior to the introduction of the lenses carried on the lens support member. However, the catalytic agent is readily removable for replacement by a user, as the catalytic agent becomes exhausted in use.

Figure 6:
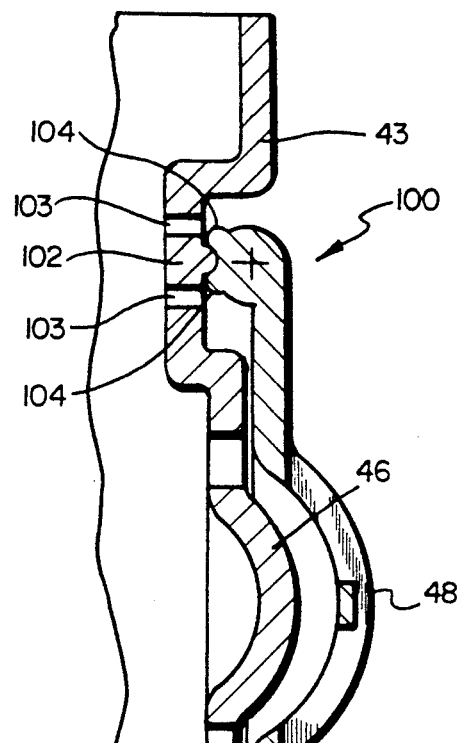
FIG. 6 is an enlarged partial sectional view of a cover portion of a lens carrier and support portion of the apparatus of the invention, showing the cover in a closed position.
Figure 7:
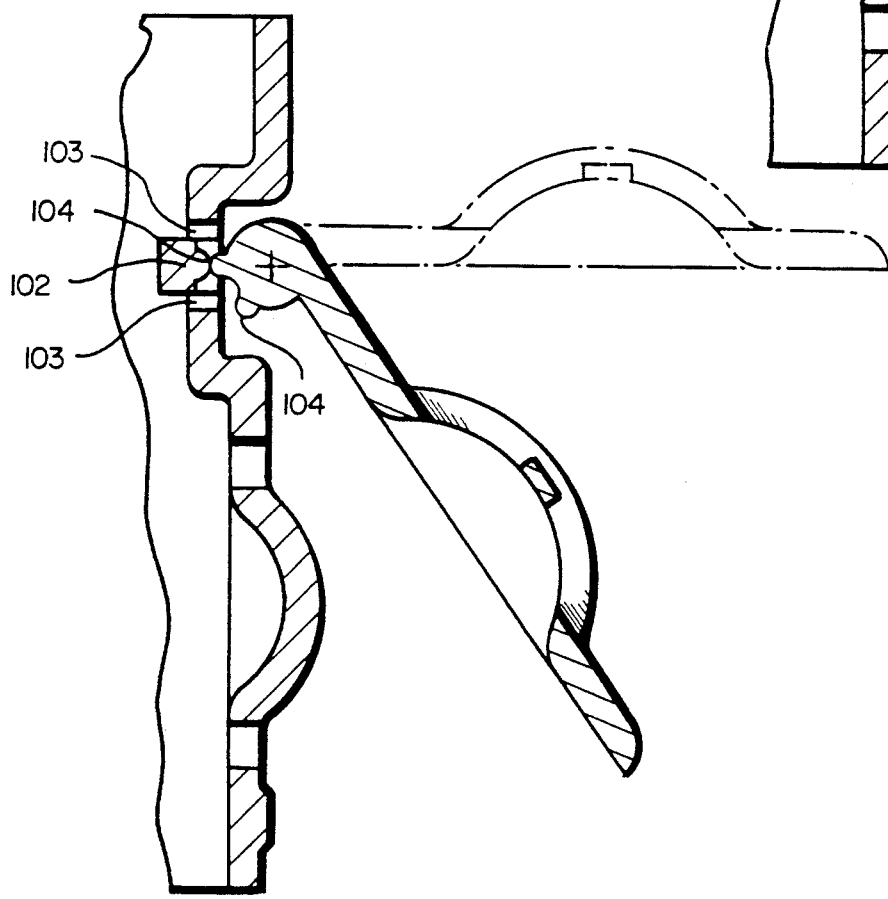
FIG. 7 is a sectional view similar to FIG. 6 and showing an intermediate position of the cover portion thereof in full line and a fully open position thereof in phantom line.

As best viewed in FIGS. 6 and 7, the lens supporting structure also includes means 100 defining a detent arrangement for holding each cover 48, 49 detented in its respective fully open and fully closed positions relative to the associated lens support member 46, 47. In the illustrated embodiment, this detenting arrangement comprises a resiliently deflectable protruding member 102, which is formed in the base 43, 45 at a position oppositely facing and aligned with an upper edge portion of the cover, at which portion the cover is hingedly coupled with the base. This protruding resilient member is formed by cutting a pair of parallel elongate thin through openings 103 in the base 43, 45 and forming a protruding, bump-like projection or portion therebetween. Cooperatively, the cover member 45 includes at least one projection or bump-like portion 104, which engages this bump-like portion during the opening and closing of the cover, and thereby defines a detented position of the cover to either side of the area or distance over which the respective projections 102, 104 engage during opening and closing thereof.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A catalyst support assembly for use with apparatus for sterilization of contact lenses; said catalyst support assembly comprising: a generally rectangular carrier configured for interfitting within a receptacle formed in a lens supporting means for contact lenses, a catalytic agent for neutralizing a hydrogen peroxide solution used in the sterilization of contact lenses carried by said carrier in such a manner that the catalytic agent is exposed at an exterior surface of said carrier for direct contact with hydrogen peroxide solution upon immersion of said catalyst support assembly in a hydrogen peroxide solution, retention means integrally formed on said carrier projecting outwardly of said carrier and configured for engaging the receptacle formed in the lens supporting means for contact lenses when said carrier is inserted into said receptacle, thereby removably mounting said catalyst support assembly relative to the lens supporting means and preventing contact of the catalytic agent with the hydrogen peroxide sterilizing solution in a reaction vessel until the catalyst support assembly mounted to the lens supporting means is immersed in a sterilizing solution in the reaction vessel for beginning a sterilizing process, to thereby prevent premature breakdown of a sterilizing solution prior to the introduction of contact lenses carried by the lens supporting means for sterilization therein.

2. A catalyst assembly according to claim 1 wherein said carrier comprises a frame-shaped member, with said retention means projecting integrally therefrom, said frame-shaped member including a central through aperture, and wherein said catalytic agent comprises a receiving body coated with a catalytic material and being disposed in said aperture formed in said frame-shaped member.

3. A catalyst assembly according to claim 1 wherein said retention means comprises a pair of spaced resilient clip members formed on said carrier and adapted to engage the receptacle in a lens supporting means with a snap fit.

4. A catalyst assembly according to claim 2 wherein said catalytic agent and said frame-shaped member are provided with complementary interengaging snap fit means for mounting said catalyst element within aperture formed in said frame-like member.

5. A catalyst assembly according to claim 1 further comprising an insertion/removal tool having first engaging means formed for engaging and subsequently releasing said carrier for mounting relative to the receptacle formed in the lens supporting means and second engaging means formed for engaging said carrier for removal thereof from the receptacle formed in said lens supporting means.

6. A catalyst support assembly for use with apparatus for sterilization of contact lenses; said catalyst support assembly comprising: a catalytic agent comprising a catalyst-receiving body of predetermined shape coated with a quantity of catalyst material for neutralizing a hydrogen peroxide solution used in the sterilization of contact lenses; a carrier member having an enlarged, generally rectangular frame-shaped body portion, and wherein said catalyst-receiving body is shaped to be engaged and supported by said frame-shaped body portion in such a manner that the catalytic agent is exposed at an exterior surface of said carrier for direct contact with hydrogen peroxide solution upon immersion of said catalyst support assembly in the hydrogen peroxide solution; and means integrally formed with said frame-shaped body portion for removably mounting said carrier member to lens supporting means, said engagement and support of said catalyst-receiving body by said frame-shaped body portion and said mounting of said carrier member to lens supporting means being adapted to prevent contact of the catalytic agent with a sterilizing solution in a reaction vessel until the lens supporting means with the catalyst support assembly mounted thereto is placed in the reaction vessel for beginning a sterilizing process, thereby to prevent premature breakdown of the sterilizing solution prior to the introduction of contact lenses carried by the lens supporting means for sterilization therein.

7. An assembly according to claim 6 wherein said means for removably mounting said carrier member to said lens supporting means further includes resilient clip engaging members, located and configured for releasable mating engagement with a lens supporting means.

8. Apparatus according to claim 6 and further including an insertion/removal tool having first engaging means formed for engaging and subsequently releasing said frame-shaped body portion for mounting thereof relative to the lens supporting means and second engaging means formed for engaging and retaining said frame-shaped body portion for removal thereof from the lens supporting means.

* * * * *

UNITED STATES PATENT AND TRADEMARK OFFICE
CERTIFICATE OF CORRECTION

PATENT NO. : 5,292,488
DATED : March 8, 1994
INVENTOR(S) : Joseph J. Cerola and Steven C. Perlaky It is certified that error appears in the above-indentified patent and that said Letters Patent is hereby corrected as shown below:

Column 7, Line 47 "in a lens" should read — in the lens —

Column 8, Line 1 "catalyst element" should read — catalyst agent —

Column 8, Line 2 " frame-like" should read — frame-shaped —

Signed and Sealed this

Fourth Day of October, 1994

Attest:

BRUCE LEHMAN

*Attesting Officer*     *Commissioner of Patents and Trademarks*